United States Patent
Allan et al.

(10) Patent No.: US 9,504,730 B2
(45) Date of Patent: Nov. 29, 2016

(54) METHOD OF ACHIEVING A THYMOSIN BETA 4 CONCENTRATION IN A HUMAN PATIENT

(75) Inventors: Christian B. Allan, Brookeville, MD (US); William Walton, Falls Church, VA (US)

(73) Assignee: REGENERX BIOPHARMACEUTICALS, INC., Rockville, MD (US)

( * ) Notice: Subject to any disclaimer, the term of this patent is extended or adjusted under 35 U.S.C. 154(b) by 155 days.

(21) Appl. No.: 13/876,767

(22) PCT Filed: Sep. 29, 2011

(86) PCT No.: PCT/US2011/053907
§ 371 (c)(1),
(2), (4) Date: Mar. 28, 2013

(87) PCT Pub. No.: WO2012/044783
PCT Pub. Date: Apr. 5, 2012

(65) Prior Publication Data
US 2013/0203684 A1 Aug. 8, 2013

Related U.S. Application Data

(60) Provisional application No. 61/388,173, filed on Sep. 30, 2010.

(51) Int. Cl.
*A61K 38/00* (2006.01)
*C07K 16/00* (2006.01)
*A61K 38/17* (2006.01)
*A61K 38/32* (2006.01)

(52) U.S. Cl.
CPC ........... *A61K 38/1709* (2013.01); *A61K 38/32* (2013.01)

(58) Field of Classification Search
None
See application file for complete search history.

(56) References Cited

U.S. PATENT DOCUMENTS

| | | |
|---|---|---|
| 5,578,570 A | 11/1996 | Goldstein et al. |
| 2004/0220111 A1 | 11/2004 | Kleinman et al. |
| 2006/0263360 A1 | 11/2006 | Goldstein |
| 2006/0264360 A1 | 11/2006 | Girardi et al. |
| 2009/0023663 A1 | 1/2009 | Kleinman et al. |
| 2009/0298758 A1 | 12/2009 | Nie et al. |
| 2010/0048474 A1 | 2/2010 | Sosne et al. |

FOREIGN PATENT DOCUMENTS

| | | |
|---|---|---|
| WO | 03/020215 A2 | 3/2003 |
| WO | 2007/084544 A2 | 7/2007 |
| WO | WO 2007084544 A2 * | 7/2007 |

OTHER PUBLICATIONS

Gumbo et al., "Selection of a Moxifloxacin Dose That Suppresses Drug Resistance in *Mycobacterium tuberculosis*, by Use of an In Vitro Pharmacodynamic Infection Model and Mathematical Modeling," J. Infectious Dis. 190:1642-1651 (2004).*
Ruff et al., "A randomized, placebo-controlled, single and multiple dose study of intravenous thymosin beta 4 in healthy volunteers," Ann. NY Acad. Sci. 1194:223-229 (May 2010).*
Ruff et. al. Ann. N.Y. Acad. Sci. 1194 223-229, ESSN 0077.-892, Apr. 2010.*
Gumbo et. al. The Journal Infectious Diseases, 190:1642751, 2004.*
D. Ruff et al., "A randomized, place-controlled, single and multiple dose study of intravenous thymosin β4 in healthy volunteers," Annals of the New York Academy of Sciences, vol. 1194, 2010, pp. 223-229.
T. Gumbo et al.: "Selection of a Moxifloxacin Dose that Suppresses Drug Resistance in *Myobacterium tuberculosis*, by Use of an In Vitro Pharmacodynamic Infection Model and Mathematical Modeling," Journal of Infection Diseases, vol. 190, 2004, pp. 1642-1651.
C. Palerm et al.: "Prandial Insulin Dosing Using Run-to-Run Control," Diabetes Care, vol. 30, No. 5, May 2007, pp. 1131-1136.
K. Malinda et al.: "Thymosin β4 Accelerates Wound Healing," The Journal of Investigative Dermatology, vol. 113, No. 3, Sep. 1999, pp. 364-368.
D. Crockford: "Developement of Thymosin β4 for Treatment of Patients with Ischemic Heart Disease," Annals of the New York Academy of Sciences, vol. 1112, 2007, pp. 385-395.
S. Dunn et al.: "Treatment of chronic nonhealing neurotrophic corneal epithelial defects with thymosin β4," Annals of the New York Academy of Sciences, vol. 1194, 2010, pp. 199-206.

* cited by examiner

*Primary Examiner* — Jeanette Lieb
(74) *Attorney, Agent, or Firm* — Rothwell, Figg, Ernst & Manbeck, P.C.

(57) ABSTRACT

The present invention provides embodiments which involve methods of providing a predetermined concentration of thymosin beta 4 (TB4) at a predetermined time, t, in a body portion of a live human patient. The methods can include determining a thymosin beta 4 treatment dosage (D) using Formula I: $C=(A)D \cdot t^{-B}$, wherein C is the predetermined concentration at time t, in ng/mL, D is the dosage of thymosin beta 4 administered in mg, t is the time elapsed after administration of dosage D in hours, A is about 30 to about 38, and B is about 0.5 to about 1; and administering the dosage (D) of thymosin beta 4 to the patient. Formula I may be, for example, $$C=(35.6)D \cdot t^{-0.754} \quad \text{(Formula II)}.$$

23 Claims, No Drawings

METHOD OF ACHIEVING A THYMOSIN BETA 4 CONCENTRATION IN A HUMAN PATIENT

CROSS REFERENCE TO RELATED APPLICATIONS

This application is a 35 U.S.C. §371 National Phase Entry Application from PCT/US2011/053907, filed Sep. 29, 2011, and designating the United States, which claims the benefit of U.S. Provisional Patent Application No. 61/388,173 filed Sep. 30, 2010, which is incorporated herein in its entirety.

BACKGROUND OF THE INVENTION

1. Technical Field

The invention relates to the field of medicinal treatment and in particular to methods for providing a pharmaceutical dosage of thymosin beta 4 to a patient.

2. Description of the Background Art

Thymosin beta 4 (TB4) initially was identified in the thymus. It is a 43-amino acid polypeptide, now known to exist in a number of tissues throughout the body. Several roles have been ascribed to this peptide, and it has been found to be useful in treating a number of conditions where immune modulation, endothelial cell differentiation and migration, T cell differentiation, actin sequestration or angiogenesis would be desirable. For example, TB4 has been used to accelerate wound healing. The amino acid sequence of TB4 is disclosed in U.S. Pat. No. 4,297,276, the disclosures of which are incorporated by reference herein.

Obtaining a desired concentration suitable for treatment is difficult when the half-life of TB4 is not great. In particular, dosage administration is not very effective in cases where the dose administered produces a high initial TB4 concentration of the drug which is far greater than the desired concentration and where the concentration rapidly decreases. Frequent re-dosing often is necessary, creating large swings in TB4 concentration. This results in both an inefficient treatment and the dangers inherent with fluctuating or unpredictable concentrations of an active compound.

SUMMARY OF THE INVENTION

In accordance with the present invention, a method of providing a desired concentration of administered thymosin beta 4 (TB4) in a body portion of a live human patient in need thereof, at a predetermined time t, is comprised of determining a thymosin beta 4 treatment dosage (D) using Formula I $$C=(A)D \cdot t^{-B} \quad \text{(Formula I)},$$

wherein C is the predetermined concentration at time t, in ng/mL, D is the dosage of thymosin beta 4 to be administered to the live human patient in mg, t is the time elapsed after administration of dosage D in hours, A is about 30 to about 38, and B is about 0.5 to about 1. The present invention further comprises administering the dosage (D) of thymosin beta 4 to the live human patient so as to achieve the desired concentration of administered thymosin beta 4 in the body portion.

DETAILED DESCRIPTION OF EMBODIMENTS OF THE INVENTION

When a large dose of thymosin beta 4 (TB4) is administered to a patient, such that the concentration produced is higher than needed for treatment or efficient treatment, the drug may be degraded more quickly, may not be effectively used by the patient, may result in waste of TB4 or may possibly even result in unexpected side effects related to overdose. When the dose administered provides thymosin beta 4 concentrations that are too low for optimum efficiency, the patient may receive an inadequate dose and re-dosing may be required at frequent intervals, reducing compliance and effectiveness. An ideal dosing regimen consistently maintains thymosin beta 4 concentrations at a specific desired level or within a specific desired range which is effective to treat the patient, but which also minimizes the total amount of drug which is administered over the treatment period. There is a need in the art for improved methods to determine an effective dose of thymosin beta 4 in a patient which can avoid waste in the form of unnecessary over-administration and in the form of inadequate and ineffective under-administration.

Embodiments of the present invention provide a method of achieving a predetermined concentration of thymosin beta 4 in a body portion of a live human patient, e.g., a human patient in need of treatment. Certain embodiments of the present disclosure provide a method of achieving a predetermined fluid concentration of thymosin beta 4 in a fluid portion of a live human patient. Other embodiments include a method of achieving a predetermined liquid concentration of thymosin beta 4 in a liquid portion of a live human patient. In another embodiment, the present disclosure provides a method of achieving a predetermined blood concentration of thymosin beta 4 in a live human patient. In another embodiment, the present disclosure provides a method of achieving a predetermined plasma concentration of thymosin beta 4 in a live human patient. The ability to determine the dosage needed to achieve the desired concentration of thymosin beta 4 is advantageous because it provides an effective therapeutic benefit for the particular patient and also avoids the waste of an expensive biological product through over-dosing.

The term "patient" as used herein means any live human person to whom thymosin beta 4 can be administered.

The term "body portion" as used herein denotes any anatomical space, tissue or region of the body, including body fluids and secretions, and includes but is not limited to any natural or artificially created body cavity or space, for example: abdominal cavity, buccal cavity, cerebral cavity, gastric cavity, gingival space, intra-articular space, nasal cavity, oral cavity, pelvic cavity, pericardial space, peritoneal cavity, pleural cavity, subarachnoid space, subcutaneous space, urinary bladder cavity, uterine cavity, vaginal cavity; or a tumor capsule, or any surgically created space (for example the space created by surgical removal of a tumor or abscess, surgical debridement of tissue and the like) or any space or area occupied by a tumor, abscess, diseased tissue, implant, prosthesis or any foreign body.

The term "body portion" includes any tissue of the body, for example but not limited to: breast tissue, cardiovascular tissue, central nervous system tissue, colon tissue, connective tissue, endometrial tissue, gastrointestinal tissue, heart tissue, heart valve tissue, liver tissue, muscle tissue, nasal cavity, pancreatic tissue, placental tissue, rectal tissue, renal tissue, skin tissue, urogenital tissue; and any fluid or secretion of the body, for example but not limited to: amniotic fluid, aqueous humor of the eye, blister fluid, blood, cerebrospinal fluid, lacrimal secretions, plasma, saliva, serum, synovial fluid, tear fluid, urine, vaginal secretions, vitreous humor of the eye, and wound fluid; and includes the total or entire body, for example for systemic administration to the whole body.

A therapeutic benefit of thymosin beta 4 may include at least partial prevention and/or treatment of side effects and/or adverse effects caused by the administration of another drug. In certain embodiments, thymosin beta 4 may be administered in conjunction with drugs that cause adverse effects, such as autoimmune inflammatory attack. For example, thymosin beta 4 may be administered with the drug ipilmumab to prevent side effects such as autoimmune inflammatory attack. Thymosin beta 4 may be administered before, during or after the drug is administered.

Further therapeutic benefits of thymosin beta 4 may also include the promotion of healing or at least partial prevention and/or treatment of damage, injury and/or other adverse changes in a live human patient due to one or more of the following conditions, which are not intended to be limiting:

Wound Healing and Tissue Repair
   Revitalize scar tissue
   Ameliorate wound healing disorder
   Healing and repair of damage due to:
   Atherosclerosis
   Arthritis
   Burns
   Cardiovascular disease (e.g., atherosclerosis, congestive heart failure, myocardial infarction)
   Chronic wounds
   Infection (viral, bacterial, fungal)
   Ischemia (brain, bone, heart)
   Musculoskeletal disorders
   Neurological and nerve diseases
   Neuromuscular-degenerative diseases
   Osteoporosis
   Quaternary ammonium salt exposure
   Radiation damage (UV)
   Skin grafts
   Skin lesions
   Toxic chemicals
   Trauma
     recurrent
     surgical
   Ulcers
     diabetic
     pressure
     venous
   Healing and repair in:
   Breast tissue
   Cardiovascular tissue
   Central nervous system tissue
   Connective tissue
     bone
     cartilage
     joints
   Epithelium
   Eye
     cornea
     retina
   Gastrointestinal tissue
   Liver
   Mucosa
   Muscle
   Neural tissue
     nerve
   Pancreatic islets
   Skin
     dermis
     epidermis
   Urogenital
     endometrium
     placenta
     uterus Dermal Conditions
   Dermatitis
   contact dermatitis
   atopic dermatitis
   Eczema
   Epidermolysis bullosa (healing of sores, blisters, skin degradation)
   Psoriasis
   Allergic or inflammatory reactions due to:
   Insect bites
   Irritants
   Poison ivy/oak/sumac
   Sensitizing agents
   Toxins
   Venomous reptiles and amphibians
   Treating symptoms:
   Blister
   Burn
   Induration
   Inflammation
   Itching
   Rash
   Redness Swelling
   Improving skin conditions associated with skin aging:
   Appearance
   Changes in actin ratios and turnover
   Changes in collagen and other matrix proteins
   Darkening (age spots)
   Decreased capacity to repair DNA damage
   Degeneration
   Elasticity (loss of)
   Increase in skin cancers
   Increased risk of infection
   Thinning Ophthalmic Conditions
   Elevated intraocular pressure (glaucoma)
   Dry eye syndrome (xerophthalemia) due to:
   Age
   Antibiotics
   Anti-diarrheals
   Antihistamines
   Corneal irregularities
   Diuretics
   Hormonal changes (menopause)
   Large eyes
   Meibomitis
   Neurotrophic keratitis
   Sjogren's syndrome
   Systemic lupus erythematosis
   Thyroid disease
   Uveitis
   Trauma to the eye due to:
   Chemical injury
   Contact lens wear
   Diabetes (keratopathy, retinopathy)
   Infection/inflammation
     blepharites
     conjunctivitis
     iritis
     keratitis
     meibomitis
     Mooren's ulcers optic neuritis
retinitis
scleritis
temporal arteritis
uveitis
Physical trauma
Quaternary ammonium salts (corneal thinning)
Recurrent corneal abrasion
Rheumatoid arthritis (corneal melts)
Surgery
  cataract
  epithelial debridement
  corneal resurfacing
  LASIK
  PRK
Cardiovascular Conditions
  Aging
  Apoptotic death of neurovascular cells
  C-reactive protein (cardiovascular disease risk)
  Clotting and vessel occlusion
  extracellular matrix build-up (body tissue or fluid transport vessel)
  plaque (coronary vessels following stenting or angioplasty)
  restenosis
  stenosis
  Congestive heart failure with or due to:
  Pulmonary edema
  Atherosclerosis
  Diabetes
  Obesity
  Tobacco use
  Alcohol abuse
  Cocaine use
  Developmental defect
  Heart valve defects
  Infarction
  Infection
  Ischemia
  Myocardial infarction and damage occurring at time of myocardial event
  Reperfusion injury (damage caused by increase in blood flow)
  Stroke
  Transformation of cardiac endothelium to mesenchyme (enhance or down-regulate)
  Trauma
  Other heart failure
General Conditions
  Infectious and Inflammatory Diseases
  Acne and acne vulgaris
  Acute generalized exanthematous pustulosis
  Allergic aspergillosis
  Ankylosing spondylitis
  Anthrax
  Arthritis
    crystal
    infectious
    juvenile chronic
    osteo
    psoriatic
    reactive
    rheumatoid
  Asthma
  Behcet's disease
  Beret's disease
  Bovine spongiform encephalopathy
  Bronchiolitis
  Bronchiolitis obliterans organizing pneumonia
  Chronic bronchitis
  Chronic obstructive pulmonary disease
  Chirg-Strauss syndrome
  Cholangitis
  Colic
  Colitis and ileitis
  Cranial arteritis
  Creutzfeld-Jakob disease
  Crohn's disease
  Cryptogenic pulmonary eosinophilia
  Dermatitis
    atopic
    contact and allergic contact
    seborrheic
    stasis
  Eczema
  Emphysema
  Epidermolysis bullosa
  Erythema elevatum diutinum
  Escherichia coli
  Fibrosing alveolitis
  Gall bladder infection
  Gastrointestinal fistulae
  Gingivitis
  Graft rejection
  Graft versus host disease
  Helicobacter pylori
  Hemolytic anemia
  Hypersensitivity pneumonitis
  Idiopathic thromocytopenic purpura
  Inflammatory bowel disease
  Job's syndrome
  Leprosy
  Lung inflammation
  Lupoid hepatitis
  Malaria
  Methocillin-resistant Staphylococcus aureus (MRSA)
  Netherton's syndrome
  Obstructive airway diseases
  Pancreatitis
  Periodontal disease (aggressive, chronic, necrotizing)
  Peritonitis
  Pneumocysitis carinii pneumonia
  Pneumonia
  Polyarteritis nodosa
  Polymyalgia rheumatica
  Pouchitis
  Psoriasis
  Pustular lesions
  Pyoderma gangrenosum
  Regional enteritis
  Sarcoidosis
  Septic shock
  Sinusitis
  Sjogren's syndrome
  Sweet's syndrome
  Subcorneal pustular dermatosis
  Systemic lupus erythematosus
  Tissue reaction to implanted prostheses
  Tuberculosis
  Ulcerative colitis
  Ulcers
  Urticaria
  Vancomycin-resistant Enterococcus (VRE)
  Vasulitis hypersensitivity
  allergic cutaneous
Wegener's granulomatosis
Neuro-, Muscular- and Neuromuscular Diseases
Alcoholism
Alexander's disease
Alper's disease
Alzheimer's disease
Amyotrophic lateral sclerosis
Ataxia telangiectasia
Autism
Batten disease
Canavan disease
Cockayne syndrome
Corticobasal degeneration
Frontotemporal lobar degeneration
Huntington's disease
HIV-associated dementia
Kennedy's disease
Krabbe's disease
Lewy body dementia
Machado-Joseph disease
Multiple sclerosis
Muscular dystrophy (Duchenne, Becker)
Myasthenia gravis
Narcolepsy
Neuroborreliosis
Neurodegenerative and demyelinating diseases
Niemann Pick disease
Parkinson's disease
Pelizaeus-Merzbacher disease
Pick's disease
Primary lateral sclerosis
Prion diseases
  transmissible spongiform encephalopathies
  bovine spongiform encephalopathy
  Creutzfeld-Jakob disease
Progressive supranuclear palsy
Refsum's disease
Sandhoff's disease
Schilder's disease
Subacute combined degeneration of spinal cord
Spinocerebellar ataxia
Spinal muscular atrophy
Steele-Richardson-Olszewski disease
Stroke
Tabes dorsalis
Traumatic brain injury
Cell Proliferative Disorders
Cancer
Diabetic retinopathy
Leukemia
Lymphoma
Multiple myeloma
Neovascular glaucoma
Psoriasis
Other Uses
Early pregnancy maintenance
Fibrotic tissue disorders
Osteoporosis
Protect tissue from UV radiation damage
Restore impaired T-lymphocyte blastogenic response
Sclerotic disorders
Wound healing disorders
Uses to Increase
  axonal myelination
  brain remodeling at locations of brain injury
  cell migration
  cellular proliferation in adult brain
  collagen IV
  differentiation of neural progenitor cells into mature glia
  differentiation of neural progenitor cells into mature neurons
  elastin
  migration of neural progenitor cells
  migration/differentiation of oligodendrocyte progenitor cells
  myelination of damaged axons
  neural progenitor cell proliferation
  nerve regeneration and/or brain remodeling
  neurite outgrowth
  neuron survival
  production of L1
Uses to Inhibit
  angiogenesis (in cancer)
  apoptosis in a tissue
  ILBa phosphorylation
  inflammation in a tissue
  inflammatory responses
  NF-kappaB-mediated activation and translocation
  tissue cytotoxicity
  UV radiation damage A physician or health care provider may first determine a desired concentration of thymosin beta 4 (or a desired increase in concentration of thymosin beta 4 from an existing level) in a body portion of a live human patient in need of treatment. The physician or health care provider may then calculate the dosage necessary to achieve the desired concentration using the formula:

$$C = (A)D \cdot t^{-B} \quad \text{(Formula I)},$$

or $$D = C/(A)(t^{-B}) \quad \text{(Formula IA)},$$

wherein C is the predetermined thymosin beta 4 concentration to be provided in ng/mL, D is the dosage of thymosin beta 4 administered in mg, t is the time elapsed after administration of an initial dosage of thymosin beta 4 in hours (t is treated as a constant in this equation), A is about 30 to about 38, and B is about 0.5 to about 1. According to one embodiment, the formula is $$C = (35.6)D \cdot t^{-0.754} \quad \text{(Formula II)}.$$

Time, t, may be 1, and D may equal C/35.6.

The above formulas were developed by analysis of data from human patients who had been administered different dosages of thymosin beta 4. The frequency of dosing needed between dosages to achieve the desired concentration over time, multiplied by the dosage, gave the total drug administered in a 24-hour period. The dosage that maintained the required concentration with the lowest total drug administered was termed the most efficient. See Exampe I, below.

Based on the data collected, concentrations of TB4 in the body portion follow (especially soon after administration, with a decreasing correlation over time) a power function. An estimation of the concentration of thymosin beta 4 at 1 hour was determined using this model with an average within 10% of the experimental mean for the concentrations tested. The concentrations in the tested patients at 1 hour give an approximate range that can be efficiently maintained because the concentrations at about 1 hour are approximately 15% of the initial concentration (mean 14.7%, median 13.3%). The concentration found in human patients at 5 minutes after initial administration intravenously was defined as the initial concentration, and as $C_{max}$, i.e. the maximum concentration achieved after administration of a dose. For the calculations made in the studies, the range of concentration which is the effective and desired dose was assumed to be 5-25% of this initial concentration ($C_{max}$). In general, intervals between intravenous treatment times of about an hour also are the most reliably efficient in achieving and maintaining a particular concentration. Therefore, in certain embodiments, when calculating dosage using Formula I or Formula II, t may equal about 1. The concentration which is achieved with a particular dosage of thymosin beta 4 at 5 minutes ($C_{max}$) can be found using Formula I by calculating C using the particular dosage (D) and 0.083 hours (5 minutes) as t.

Using Formula II, concentration at 1 hour is (35.6)D. In certain embodiments, the formula gives the concentration with an average error of about 10%, calculated against the experimental mean from in vivo patient data. Formulas I and II where t=1, therefore, provide a reasonable estimation of a concentration that is an acceptable and effective concentration to provide therapeutic treatment. The average concentration at a time of 1 hour after administration from the experimental data was 15.7%±1.32% (SD) of $C_{max}$. Therefore, without wishing to be bound by theory, assuming 5-25% of the initial (5-minute) concentration is an effective and efficient concentration range for a particular treatment, and that the concentration at a time of one hour is about 15% of the initial concentration ($C_{max}$), then the treatment concentration range would fall within (A)D±0.67(A)D, or from about 0.33(A)D to about 1.67(A)D.

The actual desired concentration to be achieved in a body portion of a live human patient for treatment of a condition is determined by a physician and may depend on many factors known in the art, such as the indication (disease to be treated) for which the thymosin beta 4 is to be administered, the patient's size, gender, and age, other disease conditions present in the patient (e.g., autoimmune disease, diabetes, renal disease), the presence of neutralizing antibodies to TB4 in the patient, endogenous or pre-existing levels of TB4, and general metabolism. Generally these concentrations will range from about 1 ng/mL to about 10 mg/mL or about 200 pM to about 2 mM. In other embodiments, concentrations range from about 10 ng/mL to about 1 mg/mL, about 10 ng/mL to about 100 μg/mL, about 10 ng/mL to about 10 μg/mL, or about 100 ng/mL to about 1 μg/mL.

With respect to the levels for treatment of cardiac diseases, certain embodiments will be in about a 6 mg/kg to 18 mg/kg range for dosing (420 mg and 1260 mg unit dose, respectively), which correspond to Cmax levels of about 90,000-350,000 ng/mL.

The range of time over which the formulas are useful is about 5 minutes to about 3 hours (e.g., about 30 minutes to about 2 hours, for example, about 1 hour). According to certain embodiments, the formulas may be used with t=about 0.67 to about 1.5 hours, for example, about t=1. When calculating values using times of 1.5 hours or greater, the formulas may be those wherein A=about 30 and B=about 0.8 to about 1. According to certain embodiments, for times of 1.5 hours or greater and especially for times of 2 hours or greater, A may equal about 30 and B may equal about Administration of thymosin β4 to a body portion can be achieved by injection (including intravenous injection, subcutaneous injection, intramuscular injection, intraperitoneal injection, direct local injection) into the body portion, infusion, osmotic pump and the like, or by other means such as topical application to a wound or to any external or internal body surface, transdermal administration, oral administration, rectal administration, vaginal administration, ocular administration, buccal administration, and the like. Formulations for use can take any convenient form, such as, for example, sterile injectable liquids, topical creams and ointments, transdermal patches, eye drops, oral rinses, irrigation solutions and other liquids, gels, or semi-solids for topical administration to a body surface or body compartment, or any acceptable pharmaceutical formulation or dosage form known in the art.

EXAMPLES

Example 1

Analysis of TB4 Concentration Data

Treatment regimens to maintain a given dose (data summary):

| Infusion dosage per dose | Frequency of administration | Total TB4 required for 24 hour treatment |
|---|---|---|
| Concentration > 1000 ng/mL in blood | | |
| *42 mg | 2 hours | 504 mg |
| 140 mg | 3 hours | 1120 mg |
| 420 mg | 6 hours | 1680 mg |
| 1260 mg | 9 hours | 3360 mg |
| Concentration > 5000 ng/mL in blood | | |
| 42 mg | 10 minutes | 6048 mg |
| *140 mg | 1 hour | 5040 mg |
| *420 mg | 2 hours | 5040 mg |
| 1260 mg | 4 hours | 7560 mg |
| Concentration > 10000 ng/mL in blood | | |
| 42 mg | 5 minutes | 12096 mg |
| *140 mg | 20 minutes | 10080 mg |
| *420 mg | 1 hour | 10080 mg |
| *1260 mg | 3 hours | 10080 mg |
| Concentration > 20000 ng/mL in blood | | |
| ~42 mg | n/a | n/a |
| 140 mg | 10 minutes | 20160 mg |
| *420 mg | 40 minutes | 15120 mg |
| *1260 mg | 2 hours | 15120 mg |
| Concentration > 40000 ng/mL in blood | | |
| ~42 mg | n/a | n/a |
| ~140 mg | n/a | n/a |
| 420 mg | 10 minutes | 60480 mg |
| *1260 mg | 1 hour | 30240 mg |

~indicates first dose does not bring TB4 concentration that high
*indicates the most efficient treatment (as determined by total required)

Example 2

Thymosin Dosage Regimens

A patient in need of thymosin beta 4 treatment with a concentration of 10,000 ng/mL exogenous thymosin beta 4 is administered thymosin beta 4 according to a dosage schedule wherein D and t are calculated using $C=(35.6)D*t^{0.754}$.

A patient in need of thymosin beta 4 treatment with a concentration of 10,000 ng/mL exogenous thymosin beta 4 with a 1-hour dosing frequency is administered $D=C/(A)t^{-B}=10{,}000$ ng/mL/(35.6)$(1^{-0.75}$ h)=281 mg thymosin beta 4.

Example 3

A patient in need of thymosin beta 4 treatment with a concentration of 10,000 ng/mL exogenous thymosin beta 4 using 200 mg unit dosage forms of thymosin beta 4 is administered one dosage form about every $t=(C/DA)^{(-1/B)}$ =10,000 ng/mL/((35.6)(200 mg))$^{(-1/0.754)}$=0.637 hours.

Thymosin beta 4 is available in single-use vials containing, for example, 200 mg per vial, to maintain sterility. A patient in need of thymosin beta 4 treatment with a concentration of 10,000 ng/mL exogenous thymosin beta 4 is administered thymosin beta 4 according to a dosage schedule wherein t is calculated using $\log_B(AD/C)$, the equation can be used to determine at what time (t) to administer thymosin beta 4.

t=10,000 ng/mL/((35.6)(200 mg))$^{(-1/0.754)}$=0.637 hours (~38 minutes).

The invention claimed is:

1. A method of treating a human patient with a desired concentration of administered thymosin beta 4 (TB4) in a body portion of a live human patient in need thereof, at a predetermined time t elapsed after administration of dosage D in hours, which comprises:
administering by injection or infusion a dosage (D) of thymosin beta 4 to said live human patient so as to achieve a desired concentration, C, of TB4 in said body portion of said live human patient at a time (t), wherein said dosage (D) is calculated as $D=C/(A)(t^{-B})$, wherein C is the selected desired concentration at time t, in ng/mL, D is the dosage of thymosin beta 4 to be administered to said live human patient in mg, t is the selected time elapsed after administration of dosage D in hours, A is about 30 to about 38, and B is about 0.5 to about 1.

2. The method of claim 1 which comprises further administering said dosage (D) of thymosin beta 4 to said live human patient at intervals of time t.

3. The method of claim 1 wherein C is about 100 ng/mL to about 100,000 ng/mL thymosin beta 4.

4. The method of claim 1 wherein C is about 500 ng/mL to about 50,000 ng/mL thymosin beta 4.

5. The method of claim 1 wherein C is about 1000 ng/mL to about 40,000 ng/mL thymosin beta 4.

6. The method of claim 1 wherein C is about 5000 ng/mL to about 10,000 ng/mL thymosin beta 4.

7. The method of claim 1 wherein t is about 0.083 hour to about 3 hours.

8. The method of claim 1 wherein t is about 0.5 hour to about 2 hours.

9. The method of claim 1 wherein t is about 1 hour.

10. The method of claim 1 wherein A is about 31 to about 37.

11. The method of claim 1 wherein A is about 32 to about 36.

12. The method of claim 1 wherein A is about 33 to about 36.

13. The method of claim 1 wherein A is about 35.6.

14. The method of claim 1 wherein B is about 0.6 to about 0.9.

15. The method of claim 1 wherein B is about 0.7 to about 0.8.

16. The method of claim 1 wherein B is about 0.75.

17. The method of claim 1 wherein B is about 0.754.

18. The method of claim 1 wherein $C=(35.6)D\cdot t^{-0.754}$.

19. The method of claim 18 which comprises further administering said dosage (D) of thymosin beta 4 to said live human patient at intervals of time t.

20. The method of claim 1 wherein said thymosin beta 4 is administered in conjunction with another drug, wherein said thymosin beta 4 is administered before, during or after said drug.

21. A method of treating a human patient with a desired concentration, C, of administered thymosin beta 4 (TB4) in a body portion of a live human patient in need thereof, at a predetermined time, t elapsed after administration of dosage D in hours, which comprises:
administering by injection or infusion a selected dosage (D) of thymosin beta 4 to said live human patient so as to achieve said desired concentration, C, of administered thymosin beta 4 in said body portion at time (t), wherein t is calculated as $\log_B(AD/C)$ wherein C is the selected desired concentration at time t, in ng/mL, D is the selected dosage of thymosin beta 4 to be administered to said live human patient in mg, A is about 30 to about 38, and B is about 0.5 to about 1.

22. A method of treating a human patient by maintaining TB4 concentration, C, within an efficient TB4 concentration range in a body portion of a live human patient in need thereof, over time, comprising:
(a) maintaining a target TB4 concentration within said efficient TB4 concentration range by administering TB4 to said live human patient by calculating (1) the dosage amount to be administered, D, and (2) the amount of time elapsed after said dosage amount, D, is administered, t, according to Formula I:

$$C=(A)D\cdot t^{-B} \quad \text{(Formula I)},$$

wherein C is a target TB4 concentration in ng/mL, wherein D is the treatment dosage to said live human patient in mg, wherein t is the time elapsed after administration of TB4 to said live human patient in hours, wherein A is about 30 to about 28, and wherein B is about 0.5 to about 1;
(b) administering by injection or infusion said treatment dosage, D, of TB4 to said live human patient at time, t, so as to achieve said target concentration of administered TB4; and
(c) repeating (a) and (b) to maintain the concentration of TB4 in said body portion within ±10% of said target concentration, C.

23. The method of claim 1, further comprising repeating said administration of TB4.

* * * * *